United States Patent [19]

Davis

[11] 4,031,204

[45] June 21, 1977

[54] FELINE VIRAL RHINOTRACHEITIS VACCINE AND COMBINATION FELINE VIRAL RHINOTRACHEITIS-CALICIVIRUS VACCINE PREPARED THEREFROM

[75] Inventor: Eldon Davis, Lincoln, Nebr.

[73] Assignee: Norden Laboratories, Inc., Lincoln, Nebr.

[22] Filed: Mar. 30, 1976

[21] Appl. No.: 671,792

[52] U.S. Cl. .................................. 424/90; 195/1.2; 195/1.4; 424/89
[51] Int. Cl.² ................ A61K 41/00; A61K 39/12; C12K 7/00
[58] Field of Search ................ 424/90; 195/1.2, 1.4

[56] References Cited

UNITED STATES PATENTS

| | | | |
|---|---|---|---|
| 3,259,546 | 7/1966 | Polley | 195/1.2 |
| 3,914,408 | 10/1975 | Mebus | 424/90 |

*Primary Examiner*—Sam Rosen
*Attorney, Agent, or Firm*—Janice E. Williams; William H. Edgerton; Alan D. Lourie

[57] ABSTRACT

A modified live feline viral rhinotracheitis vaccine is prepared by treating with ultraviolet light a feline viral rhinotracheitis virus which has been subjected to chemical treatment with mutagens. A combination feline viral rhinotracheitis-calicivirus vaccine is prepared by combining a modified live feline viral rhinotracheitis virus and naturally-occurring calicivirus.

28 Claims, No Drawings

FELINE VIRAL RHINOTRACHEITIS VACCINE AND COMBINATION FELINE VIRAL RHINOTRACHEITIS-CALICIVIRUS VACCINE PREPARED THEREFROM

This invention relates to the art of vaccines. In particular, the invention relates to a modified live feline viral rhinotracheitis vaccine, to a combination feline viral rhinotracheitis-calicivirus vaccine prepared therefrom and to processes for preparing and using such vaccines.

Feline viral rhinotracheitis (FVR) disease was first described by Crandell and Maurer, *Proc. Soc. Exptl. Biol.* J *Med.*, 97:487–490 (1958). The virus is a herpesvirus and is responsible for approximately 40 percent of the upper respiratory infections of cats.

A vaccine against FVR is described by Bittle and Rubic, *Am. J. Vet. Res.*, 36:89–91 (1975) and Scott, *Feline Practice*, Jan.–Feb. 1975, pgs, 17–22. That vaccine was obtained by serial passage of a virulent FVR virus 81 times in primary feline kidney tissue culture and then 17 times in a feline diploid tongue cell line. German Offenlegungsschrift No. 25,12,903 also discloses a FVR vaccine prepared from virulent FVR virus by serial passage in feline tissue cultures.

The prior art vaccines are administered intramuscularly at the normal body temperature of the cat (39° C), at which temperature the virus is unable to grow and behaves essentially as a killed vaccine. During injection of the vaccine, the respiratory tract of the animal must be protected from infection by the virus. Other disadvantages of the prior art vaccines are that multiple doses are recommended to effect immunity and that vaccination of pregnant female animals is not recommended.

The present invention consists of a safe and effective vaccine for prophylaxis of animals belonging to the genus felidae against virulent FVR infection, which vaccine can be administered intranasally such as by dropping or spraying a suitable vaccine solution into the nasal passages, intraocularly by absorption of vaccine solution dropped into the eyes into the susceptible tissues with nasal-lachrymal duct drainage into the nose and throat areas or by injection of a suitable solution of the vaccine. The intranasal and a combination intranasal-intraocular (one drop in each eye with the remainder dropped into the nose) routes of administration are preferred. Preferably, from about $10^{5.0}$ TCID$_{50}$ to about $10^{8.0}$ TCID$_{50}$ per dose is administered. The vaccine of this invention may also be administered to pregnant female animals with no abortion or teratogenic effects. Processes for preparing and using such vaccines are also considered as objects of this invention.

The vaccine of this invention is prepared by exposing to ultraviolet light a FVR virus which has itself been subjected to chemical treatment with mutagens. In its preferred form, the process of preparation consists of exposing to ultraviolet light a FVR virus which has been subjected to chemical mutation with 5-fluorouracil, 5-fluorodeoxyuridine and bromodeoxyuridine so that the virus grows well at 30° C ± 2° C, but not as well at 37° C.

Any virulent FVR virus may be used in the treatment with the chemical mutagens. The virus may be isolated in a suitable host cell culture and propagated and maintained in media known to the art. Suitable host cell cultures include any cells cultured from the genus felidae such as kidney, tongue, tracheae, turbineate, tensil and lung. Feline kidney cells are preferred. The virus is then subjected to chemical mutagens (DNA inhibitors) after a pretreatment of the substrate cells with 5-fluorouracil, 5-fluorodeoxyuridine, bromodeoxyuridine or any other known DNA inhibitor. A mixture of 5-fluorouracil, 5-fluorodeoxyuridine and bromodeoxyuridine is preferred to mutate the virus. The virus cultures are then cloned at 30° C ± 2° C, preferably at 31° C, to purify the virus and those that grow well at that temperature are used for repeated treatment. The mutation treatment is repeated for from 12 to 36 hours, about 24 hours being preferred.

Virus obtained from the mutation treatment, ATCC No. VR 814, is then subjected to ultraviolet light until from about 90% to about 99%, preferably from about 95% to about 99% and advantageously about 99%, of the virus particles are killed. Before being administered to cats, the remainder of the ultraviolet treated virus is cloned at 31° C. Advantageously, the cloned virus is serially passaged at 30° C ± 2° C from one to about 12 times, 10 to 12 times being preferred. Any clone of the virus may also be treated repeatedly with ultraviolet light, preferably one additional treatment, and cloned before final passage and/or use.

Although virus growth (both chemically mutated virus and ultraviolet treated virus) is optimum at 31° C, the virus may also be grown at temperatures up to and including about 37° C. Growth of the virus is naturally restrictive at 39° C. Preferably, growth of the virus is carried out at 30° C ± 2° C.

DETAILED DESCRIPTION OF THE VACCINE

A FVR virus used to make the modified virus was cultured from a three-month old cat. The virus was isolated during a routine study of upper respiratory infections and came from the throat of a cat with no clinical symptoms of upper respiratory disease. To determine if the virus indeed was infectious for susceptible animals, it was passed once in feline kidney cells (NLKF-1) and then administered by intranasal inoculation into two SPF (specific pathogen free) cats. Anorexia, pyrexia, difficulty in breathing and sluggishness were observed from three to eight days after inoculation. Thus, it was apparent that this virus was infectious for susceptible cats and not a naturally occurring non-pathogenic variant.

The host cell used for isolation and all further studies was a stable serially plantable feline kidney cell line designated NLFK-1. Hanks' Balanced Salt Solution plus lactalbumin (HAL medium) was used for cell propagation and as maintenance medium for viral growth. The medium was supplemented with 10% foetal calf serum for cell growth and 2% for maintenance.

Exposure of the FVR to chemical mutagens was carried out according to procedures outlined by Pringle et al., *Virology* 55:495–505 (1973). A monolayer of NLFK-1 cells was exposed to 5-fluorouracil (10 mcg/ml) incorporated into serum-free HAL medium for 18 hours prior to virus infection. After the 18 hour exposure, the monolayer was washed with serum-free HAL medium and $10^2$ virus particles adsorbed for one hour at 37° C. The cells were then fed with HAL serum-free medium containing 5-fluorouracil (10 mcg/ml), 5-fluorodeoxyuridine (10 mcg/ml) and bromodeoxyuridine (5 mcg/ml). Incubation was carried out at 37° C for 24 hours. The cell monolayer was disrupted by rapid alternate freezing and thawing and the entire process repeated. After each exposure to the DNA inhibitors, the viral cultures were cloned at 31° C in 24 well Linbro plastic culture plates and only clones which grew well at 31° C were used for repeat treatment. Virus was harvested only when one clone was observable after seven days incubation. All isolated clones were cultivated at 31° C in NLFK-1 cells grown in milk dilution bottles. Titrations were made at 31° and 37° C to detect any temperature sensitive (*ts*) properties. After the first mutagen exposure, no *s* properties were detected and the mutagenic process was repeated with a clone. A clone which showed very small *ts* differences was chosen from each of four subsequent cloning procedures and subjected to further treatment. Thirty clones were obtained from the first treatment, 25 from the second, 50 from the third and 15 from the fourth.

Cloned virus from the fourth mutagenic exposure was tested in susceptible SPF cats. Each cat received approximately 0.25 ml ($10^{5.0}$–$10^{8.0}$ $TCID_{50}$/dose) of virus in each nostril and one drop of virus suspension in each eye. Throat swabs taken 3 days post-inoculation were positive for FVR. This virus was deposited in the American Type Culture Collection and given the accession number VR 814. It will be freely available on request upon issuance of this patent.

The virus obtained from the fifteenth clone of the fourth DNA-inhibitor treatment was then exposed to ultraviolet light (sterilamp). The virus was exposed in a plate having a fluid depth of 5 mm at 15 cm from the light source. Agitation during ultraviolet treatment was by magnetic bar at approximately 50 rpm. Samples were removed at three minute intervals. Ultraviolet light was particularly lethal to the FVR virus with a reduction in virus titer of approximately 99% in eight minutes. Clones of the ultraviolet treated virus which grew at 31° C after 99% of the virus particles were killed were prepared. Although any of these clones is suitable for further use, a clone having a virus titer of $10^{7.50}$ $TCID_{50}$ at 31° C and $10^{6.63}$ $TCID_{50}$ at 37° C was again exposed to ultraviolet light and clones were picked from it at 31° C. A clone having a virus titer of $10^{8.0}$ $TCID_{50}$ at 31° C and $10^{6.68}$ $TCID_{50}$ at 37° (other clones may also be used) was selected for further study and was serially passed at 31° C before administration to animals.

The viral material isolated as described above is used directly to vaccinate cats or is preferably formulated as lyophilized material, advantageously in combination with a suitable stabilizer known to the art. The lyophilized product is rehydrated by mixing with sterile water or other acceptable diluent prior to administration. All such forms of viral material suitable for vaccinating cats are considered to be within the scope of this invention.

The FVR virus altered as described above ($FVR_m$) was cultivated at 31° C in all studies. Roux and Povitsky bottles were used for stationary cultures and 10 liter roller bottles used for viral growth. An NLFK-1 cell monolayer was allowed to form in all culture vessels prior to inoculation of the $FVR_m$ virus. Although 10% foetal calf serum (pretested for BVD contamination) has been used for cell growth, the NLFK-1 cell line will grow very well with reduced serum content and in up to about 10% of other homologous or heterologous sera. The $FVR_m$ virus multiplies well in the NLFK-1 cells in the presence of 2% foetal calf serum. Virus harvest was made when cytopathogenic changes indicated maximum growth. The virus obtained from this harvest was deposited in the American Type Culture Collection and given accession number VR 815. It will be freely available on request upon issuance of this patent. This virus was used to vaccinate cats as described below.

Studies for confirmation of the identity of the virus consisted of growth in feline tissue culture with typical cytopathologic changes accompanied by type A inclusion bodies, failure to grow in cells of other species (host specificity), fluorescent antibody staining, organic solvent inactivation, growth inhibition by DNA synthesis inhibiting chemicals and neutralization by specific antiserum.

The host specificity of the FVR virus has been well established, Andrews et al., *Viruses of Vertebrates*, pp. 348–349 (1972). The $FVR_m$ virus likewise has a host cell specificity for feline established and primary cell types when compared with various rabbit, canine, bovine, equine, mouse, monkey and human cell types. The mutation which has occurred in the FVR virus to form the $FVR_m$ virus has not altered the host specificity, but has altered the virulence of the virus when introduced into the animal by the normal route of infection. Fully virulent FVR virus will not cause any type of disease in the susceptible cat when introduced by the intramuscular or intravenous routes. The respiratory tract, however, must be adequately protected during the inoculation procedure. Intravenous inoculation of as much as $10^{7.5}$ $TCID_{50}$ of virulent FVR virus, although not producing disease, will stimulate high titer of humoral antibody with one injection. Intramuscular injection with the same virus engenders only a slight humoral response with one injection.

Fluorescent antibody, obtained from the National Animal Disease Laboratory, has been used to identify the $FVR_m$ virus. Specific staining has been observed in cells infected with $FVR_m$ but not with cells infected with calicivirus.

A 20% concentration of ethyl ether has been shown to totally inactivate the $FVR_m$ virus in 18 hours. Virulent FVR virus was used as a control. A 50% chloroform concentration will inactivate totally the $FVR_m$ virus in approximately 30 minutes. These experiments indicate that the $FVR_m$ virus has an essential lipid which is extractable with organic solvents identical to the unmodified FVR virus.

Desoxycholate, a chemical known to inhibit DNA synthesis, specifically inhibits the $FVR_m$ and FVR viruses to the same degree.

Antiserum prepared in rabbits against a well established strain of FVR virus specifically inhibits the $FVR_m$ virus. This antiserum does not inhibit a calicivirus strain which is a well established pathogen of the cat.

Accelerated stability studies were performed on lyophilized samples of $FVR_m$ by combining the $FVR_m$ virus with a stabilizing fluid and incubating at 37° C for 1, 2 and 3 weeks. The stabilizer has the following composition:

| | |
|---|---|
| Solution A | |
| Pancreatic digestive casein (type M) | 40 g |
| Gelatin (Knox 250 A) | 40 g |
| Distilled Water (q.s.) | 1000 ml |
| Solution B | |
| Sucrose | 150 g |
| Distilled Water (q.s.) | 1000 ml |

Solutions A and B were combined at 1:1 concentration and added to a solution of the virus to 33⅓% total volume.

Results of the stability studies are shown in Table 1.

TABLE I

| Test Number | Virus Titer ($TCID_{50}$/ml) | | | |
|---|---|---|---|---|
| | Before Incubation | 1 Week | 2 Weeks | 3 Weeks |
| 1 | $10^{6.32}$ | $10^{6.24}$ | $10^{5.49}$ | $10^{5.76}$ |
| 2 | $10^{6.32}$ | $10^{5.69}$ | $10^{5.30}$ | $10^{5.40}$ |

From this data, it is apparent that the $FVR_m$ virus in combination with a stabilizing solution remains potent (as indicated by virus titers) for at least 3 weeks under accelerated stability studies, which is equivalent to about two years at refrigeration temperatures. Other combination ratios of $FVR_m$ virus and stabilizer may also be used provided the virus titer remains in the range of about $10^{5.0}$ $TCID_{50}$ to about $10^{8.0}$ $TCID_{50}$.

USE OF THE MODIFIED FELINE VIRAL RHINOTRACHEITIS VACCINE

The $FVR_m$ virus was tested by administering it to SPF minimal disease and conventional colony-reared cats and then challenging the cats with virulent virus. All cats were vaccinated by administering approximately 0.25 ml of virus containing fluid ($10^{5.0}$–$10^{8.0}$ $TCID_{50}$/dose) into each nostril. The vaccine was dropped into the nose while the head of the animal was held upright with the nose in as perpendicular a position as possible consistent with comfort of the animal. Alternatively, one drop of the vaccine may be dropped into each eye with the remainder being dropped into the nostrils.

Antibody titers were determined by microtiter techniques. Serum dilutions were made in two-fold steps, mixed with 50 $TCID_{50}$ of virulent virus, allowed to incubate for one hour and mixed with sufficient NLFK-1 cells to plant 8 wells in a 96 well microtiter plate. The cell-antibody-virus titrations were incubated at 37° C for 6 days and observed daily on a Leitz inverted microscope. Other well established methods in virology for incubation and determination of antibody titers may also be used.

Three weeks following vaccination, the animals were exposed to an aerosol of virulent virus. The aerosol was accomplished by use of a DeVilbiss atomizer utilizing compressed air as a vehicle. The aerosol was directed into the animal's face and consisted of $10^{7.3}$ $TCID_{50}$ of virulent virus. Control unvaccinated animals were treated in an identical manner. Daily examinations were made in an attempt to discern clinical disease. Viral isolations were attempted from throat swabs taken 3 days after challenge.

$FVR_m$ virus obtained from the second treatment with ultraviolet light described above was inoculated intranasally into two SPF cats prior to serial passage. Although these animals experienced a pyrexia for 1 to 4 days, no other symptoms of FVR were discernable.

Serial passage 10 was inoculated into four susceptible cats. The vaccination was made by the intranasal route. Serial passage 10 was inoculated into four kittens that were 3 weeks of age. No clinical disease was observed over a 9 week observation period in any of these animals. Although the four kittens had substantial antibody titers, probably maternally derived, these titers were boosted 2–4 fold after intranasal inoculation.

Minimal disease cats were obtained from Fauna Laboratories, Hudson, Mass. (now Liberty Laboratories, Liberty Corner, New Jersey) to test their reactions to the intranasal inoculation of passage 10. These animals were 12 weeks of age when received and has serum antibody titers <½. The dosage of the $FVR_m$ virus was 0.25 ml into each nostril and one drop into each eye. Serum antibody responses ranged from one-fifth to one-twentyfifth after vaccination. No signs of clinical disease were observed post-vaccination or post-challenge. The minimal disease animal is highly susceptible to FVR infection and is adequately protected when vaccinated intranasally with $FVR_m$ virus. Results of this study are given in Table 2.

TABLE 2

Reaction of Minimal Disease Cats to Intranasal $FVR_m$ Vaccination

| Cat | Serum Antibody Response Pre-Vaccination | Post-Vacinnation | Clinical Signs Post-Vaccination | Post-Challenge |
|---|---|---|---|---|
| 1 | <1/2 | 1/8 | Negative | Negative |
| 2 | <1/2 | 1/8 | Negative | Negative |
| 3 | <1/2 | 1/12 | Negative | Negative |
| 4 | <1/2 | 1/5 | Negative | Negative |
| 5 | <1/2 | — | — | F, ND, S |
| 6 | <1/2 | — | — | F, ND, S |
| 7 | <1/2 | — | — | F, ND, S |
| 8 | <1/2 | — | — | F, ND, C, S |

F = Fever
ND = Nasal Discharge
S = Sneezing
C = Conjunctivitis

To test the boostering effect of a second intranasal vaccination, five susceptible animals were given one dose and 1 month later another dose was administered. A definite boostering effect was noted following a second intranasal vaccination (Table 3).

TABLE 3

Reaction of Cats to Two Intranasal $FVR_m$ Vaccinations

| Cat | Pre-Vaccination | Serum Antibody Response Post-Vaccination 1 | Post-Vaccination 2 | Clinical Signs |
|---|---|---|---|---|
| 1 | 1/3 | 1/12 | 1/56 | Negative |
| 2 | <1/2 | 1/6 | 1/32 | Negative |
| 3 | <1/2 | 1/5 | 1/28 | Negative |
| 4 | <1/2 | 1/5 | 1/48 | Negative |

Fourteen minimal disease kittens, approximately 12 weeks of age were obtained from Liberty Laboratories and vaccinated intranasally with $FVR_m$ - passage 11. All animals had serum antibody response of <**. $FVR_m$ was adjusted to $10^{5.0}$ $TCID_{50}$/animal. In all animals, serum antibody responses ranged from one-eighth to one-twentyfourth post-vaccination. None of the animals exhibited clinical signs of disease.

Three six week old kittens and the mother queen were also vaccinated intranasally with $FVR_m$ - passage 11. The kittens and the queen were susceptible to FVR (serum antibody responses <½). Three weeks following vaccination all animals had serum antibody titers of one-twentieth or greater. Although this queen was not selected as a seronegative animal, the evidence certainly demonstrates that $FVR_m$ virus will immunize totally susceptible kittens of 6 weeks of age with no evidence of deleterious side effects.

Five back-passages of $FVR_m$ - passage 11 in totally susceptible minimal disease animals has not shown in any case a reversion to virulence. The animals were administered approximately $10^{6.5}$ $TCID_{50}$/animal of each back passage. Clinical disease was not seen and no pyrexia observed. The virus was administered intranasally and into the eyes of each of two animals at each passage.

A further aspect of this invention is a combination feline viral rhinotracheitis-feline calicivirus vaccine prepared from the $FVR_m$ virus described above and a naturally-occurring modified calicivirus capable of creating immunity.

The calicivirus used in these studies was cultured from the nasopharyngeal region of a six month old cat and was shown not to produce any manifestation of disease in susceptible animals. Studies for confirmation of identity of the virus consisted of rapid growth in feline tissue culture with typical calicivirus cytopathic changes and absence of inclusion bodies in stained preparations, no inactivation by organic solvents and neutralization by specific antiserum.

PREPARATION AND USE OF THE FELINE VIRAL RHINOTRACHEITIS-CALICIVIRUS COMBINATION VACCINE

The $FVR_m$ virus and the calicivirus were combined with stabilizer in the following proportions:

| | |
|---|---|
| 0.25 ml | $FVR_m$ virus |
| 0.25 ml | Calicivirus |
| 0.50 ml | Stabilizer |

Each 0.25 ml of virus had $10^{6.5}$ $TCID_{50}$ or greater. The stabilizer had the following composition:

| | |
|---|---|
| Solution A | |
| Pancreatic digestive casein (type A) | 4.0 g |
| Gelatin (Knox 250 A) | 4.0 g |
| Distilled water (q.s.) | 100.0 ml |
| Solution B | |
| Sucrose | 15.0 g |
| Distilled water (q.s.) | 100.0 ml |

Final stabilizer solution was prepared by adding equal portions of Solution A and Solution B. The pH was adjusted to 7.0.

Accelerated stability studies were performed on lyophilized samples of the combination product by incubating samples at 37° C for 1 week and 2 weeks. After the incubation period, the samples were rehydrated and titrated in NLFK-1 cells. Other combination ratios of $FVR_m$ virus, calicivirus and stabilizer may also be used provided the virus titer remains in the range of about $10^{5.0}$ $TCID_{50}$ to about $10^{8.0}$ $TCID_{50}$.

The lyophilized vaccine was rehydrated to 0.5 ml with sterile diluent and all cats were vaccinated by administering approximately 0.25 ml of virus containing fluid into each nostril. One drop of virus containing fluid was often placed into each eye to determine safety of the vaccine and as a test for irratation to mucous membranes. The virus was dropped into the nose while the head of the animal was held upright with the nose in as perpendicular a position as possible consistent with comfort of the animal.

To determine the effects of a feline viral rhinotracheitis-calicivirus combination vaccine when administered intranasally, cats were administered 0.5 ml of a 1:1 combination of $FVR_m$ and calicivirus viruses. These viruses had titers of $10^{7.5}$ $TCID_{50}$ for the $FVR_m$ virus and $10^{8.6}$ $TCID_{50}$ for the calicivirus. All of the animals were pre-bled and the serum from each pen pooled. Each pen consisted of at least five animals. The serum neutralization studies can be found in Table 4.

TABLE 4

Effects of $FVR_m$ and Calicivirus on Intranasal Inoculation

| Pen No. | No. cats per pen | Serum Neutralization Prevaccination (average) | | Serum Neutralization 4 Weeks Post-Vaccination | |
|---|---|---|---|---|---|
| | | Calicivirus | FVR virus | Calicivirus | FVR virus |
| A | 5 | 1/96 | 1/32 | >1/256 | 1/128 |
| B | 5 | 1/56 | 1/16 | >1/256 | 1/48 |
| C | 5 | 1/64 | 1/40 | >1/256 | 1/192 |
| D | 7 | 1/28 | 1/8 | >1/256 | 1/48 |
| E | 6 | 1/56 | 1/24 | >1/256 | 1/64 |
| F | 5 | 1/96 | 1/6 | >1/256 | 1/56 |
| G | 5 | 1/32 | 1/28 | 1/256 | 1/96 |
| H | 5 | 1/48 | 1/32 | >1/256 | 1/56 |
| I | 5 | 1/40 | 1/24 | 1/256 | 1/64 |
| J | 5 | 1/24 | 1/14 | >1/256 | 1/48 |

A combination of the two vaccine viruses profoundly influenced the serum neutralization titers without any evidence of interference when administered intranasally. All of the animals were carefully observed for indications of upper respiratory tract infection after the vaccination and none were seen. An identical control group of cats which were located in pens across a walkway demonstrated no upper respiratory tract infection during this period.

Thirty-one colony reared kittens (varying from two weeks to five months of age) were vaccinated with a combination feline viral rhinotracheitis-calicivirus vaccine. The vaccine contained $10^{6.0}$ $TCID_{50}$ of each virus per dose. In all instances but one, a significant increase in serum neutralizing titer was seen.

The abortigenic effect of the feline viral rhinotracheitis-calicivirus combination vaccine was tested in four SPF pregnant queens. The queens were approximately 30 days into gestation when a full dose of vaccine ($10^{6.5}$ $TCID_{50}$ of each virus) was administered intranasally. The queens were devoid of antibody to either virus prior to vaccination. All queens responded to the combination vaccine by developing significant antibody titers prior to parturition. Normal kittens were born to each queen and remained normal throughout the experimental study. It is apparent that the feline viral rhinotracheitis-calicivirus combination can safely be administered to pregnant queens and will not cause abortions or disease in the neonatal animals.

Four kittens born to SPF unvaccinated queens were given the feline viral rhinotracheitis-calicivirus combination vaccine at 2 weeks of age. The kittens had no prevaccination titer to either virus but developed protective titers to both viruses at three weeks post-vaccination. Thus, the feline viral rhinotracheitis-calicivirus combination vaccine may be safely administered intranasally to very young kittens.

The feline viral rhinotracheitis-calicivirus combination vaccine can be formulated and administered in the same manner as described above for the modified feline viral rhinotracheitis vaccine. The intranasal or combination intranasal-intraocular routes of administration of rehydrated lyophilized vaccine are preferred.

What is claimed is:

1. A modified live feline viral rhinotracheitis vaccine capable of inducing immunity in animals of the genus felidae without serious side effects comprising a modified live feline viral rhinotracheitis virus prepared by treating a feline viral rhinotracheitis virus which has been chemically modified by treatment with DNA inhibitor(s) so that said virus grows well at 30° C ± 2° C but not at 39° C with ultraviolet light until from about 90% to about 99% of the virus particles are killed, and a carrier therefor.

2. The modified live feline viral rhinotracheitis vaccine of claim 1 where the chemically modified feline viral rhinotracheitis virus is treated with ultraviolet light until from about 95% to about 99% of the virus particles are killed.

3. The modified live feline viral rhinotracheitis vaccine of claim 2 where the chemically modified feline viral rhinotracheitis virus is treated with ultraviolet light until about 99% of the virus particles are killed and the treated virus is then passaged at least once in cells of the genus felidae at 30° C ± 2° C.

4. The modified live feline viral rhinotracheitis vaccine of claim 3 where the ultraviolet treated virus is passaged in feline kidney cells containing from about 2% to about 10% homologous or heterologous serum at 30° C ± 2° C.

5. The modified live feline viral rhinotracheitis vaccine of claim 4 where the treated virus is passaged 10 to 12 times in stable feline kidney cells containing from about 2% to about 10% of foetal calf serum at 31° C.

6. The modified live feline viral rhinotracheitis vaccine of claim 5 where the chemically modified feline viral rhinotracheitis virus is ATCC No. VR 814.

7. The modified live feline viral rhinotracheitis vaccine of claim 1 where the virus titer is from about $10^{5.0}$ $TCID_{50}$ to about $10^{8.0}$ $TCID_{50}$ per dose.

8. A process for preparing the modified live feline viral rhinotracheitis vaccine of claim 1 which comprises treating a feline viral rhinotracheitis virus which has been chemically modified so that said virus grows well at 30° C ± 2° C but not at 39° C with ultraviolet light until from about 90% to about 99% of the virus particles are killed.

9. The process of claim 8 where the chemically modified feline viral rhinotracheitis virus is treated with ultraviolet light until from about 95% to about 99% of the virus particles are killed.

10. The process of claim 9 where the chemically modified feline viral rhinotracheitis virus is treated with ultraviolet light until about 99% of the virus particles are killed and the treated virus is then passaged at least once in cells of the genus felidae at 30° C ± 2° C.

11. The process of claim 10 where the ultraviolet treated virus is passaged in feline kidney cells containing from about 2% to about 10% homologous or heterologous serum at 30° C ± 2° C.

12. The process of claim 11 where the treated virus is passaged ten to twelve times in stable feline kidney cells containing from about 2% to about 10% of foetal calf serum at 31° C.

13. The process of claim 8 where the chemically modified feline viral rhinotracheitis virus is ATCC No. VR 814.

14. A process for preparing a further quantity of modified live feline viral rhinotracheitis virus comprising further growing a modified live feline viral rhinotracheitis virus as claimed in claim 1 in feline kidney cells at 30° C ± 2° C, said further growth being for a length of time sufficient to permit growth of a larger amount of said virus and then harvesting the resultant viral material.

15. The process of claim 14 where the modified live feline viral rhinotracheitis virus is ATCC No. VR-815.

16. The process of claim 14 where the modified live feline viral rhinotracheitis virus is grown in stable feline kideny cells containing from about 2% to about 10% of foetal calf serum at 31°.

17. A method of vaccinating animals of the genus felidae comprising administering to said animals the modified live feline viral rhinotracheitis vaccine of claim 1.

18. The method of claim 17 where the modified live feline viral rhinotracheitis vaccine is administered intranasally.

19. The method of claim 17 where the modified live feline viral rhinotracheitis vaccine is administered intraocularly.

20. The method of claim 17 where the modified live feline viral rhinotracheitis vaccine is administered both intranasally and intraocularly.

21. A combination modified live feline viral rhinotracheitis-calicivirus vaccine capable of inducing immunity in animals of the genus felidae without serious side effects comprising a modified live feline viral rhinotracheitis virus obtained as in claim 1, a vaccinal feline calicivirus and a carrier therefor.

22. A combination modified live feline viral rhinotracheitis-calicivirus vaccine capable of inducing immunity in animals of the genus felidae without serious side effects comprising a modified live feline viral rhinotracheitis virus obtained as in claim 5, a vaccinal feline calicivirus and a carrier therefor.

23. A combination modified live feline viral rhinotracheitis-calicivirus vaccine capable of inducing immunity in animals of the genus felidae without serious side effects comprising a modified live feline viral rhinotracheitis virus obtained as in claim 6, a vaccinal feline calicivirus and a carrier therefor.

24. The combination feline viral rhinotracheitis-calicivirus vaccine of claim 21 where the modified live feline viral rhinotracheitis virus and the calicivirus are present in a 1:1 ratio.

25. A method of vaccinating animals of the genus felidae comprising administering to said animals the combination feline viral rhinotracheitis-calicivirus vaccine of claim 21.

26. The method of claim 25 where the combination feline viral rhinotracheitis-calicivirus vaccine is administered intranasally.

27. The method of claim 25 where the combination feline viral rhinotracheitis-calicivirus vaccine is administered intraocularly.

28. The method of claim 25 where the combination feline viral rhinotracheitis-calicivirus vaccine is administered both intranasally and intraocularly.

* * * * *